United States Patent [19]
Zelina et al.

[11] Patent Number: 6,094,523
[45] Date of Patent: Jul. 25, 2000

[54] INTEGRAL FLASH STEAM GENERATOR

[75] Inventors: Francis Zelina, Lake City; Susan Napierkowski, Erie, both of Pa.

[73] Assignee: American Sterilizer Company, Erie, Pa.

[21] Appl. No.: 08/485,736

[22] Filed: Jun. 7, 1995

[51] Int. Cl.[7] ............... B01D 3/06; F22B 29/06; A61L 2/00
[52] U.S. Cl. .................. 392/399; 392/396; 422/298
[58] Field of Search ................ 392/399, 400, 392/401, 402, 485, 486, 496, 341, 342, 396; 219/523; 422/298, 305, 307

[56] References Cited

U.S. PATENT DOCUMENTS

| | | |
|---|---|---|
| 2,007,034 | 7/1935 | Bidwell . |
| 2,615,215 | 10/1952 | Stagner ................... 392/399 |
| 3,134,191 | 5/1964 | Davis ..................... 392/399 |
| 3,250,723 | 5/1966 | Fortney ................... 392/399 |
| 3,443,884 | 5/1969 | Linder . |
| 3,646,320 | 2/1972 | Rosatelli et al. . |
| 3,650,678 | 3/1972 | Hansen . |
| 3,675,360 | 7/1972 | Pierce .................... 392/399 |
| 3,854,032 | 12/1974 | Cooper . |
| 4,094,638 | 6/1978 | Todtenhaupt et al. . |
| 4,266,116 | 5/1981 | Bauer et al. . |
| 4,421,605 | 12/1983 | Huhta-Koivisto . |
| 4,536,258 | 8/1985 | Huhta-Koivisto . |
| 4,609,811 | 9/1986 | Danner ................... 392/399 |
| 4,642,165 | 2/1987 | Bier . |
| 4,724,824 | 2/1988 | McCoy et al. . |
| 4,733,637 | 3/1988 | Huhta-Koivisto . |
| 4,748,314 | 5/1988 | Desage . |
| 4,767,502 | 8/1988 | Santassalo et al. . |
| 4,871,115 | 10/1989 | Hessey ................... 392/396 |
| 4,917,771 | 4/1990 | Santassalo et al. . |
| 4,941,527 | 7/1990 | Toth et al. . |
| 5,068,087 | 11/1991 | Childers . |
| 5,078,976 | 1/1992 | Shibauchi et al. . |
| 5,290,511 | 3/1994 | Newman . |

FOREIGN PATENT DOCUMENTS

| | | |
|---|---|---|
| 2131695 | 6/1984 | United Kingdom . |
| WO 92/03170 | 3/1992 | WIPO . |

OTHER PUBLICATIONS

"Introducing The New AMSCO Eagle Series 180 Sterilizers"—American Sterilizer Company.

Primary Examiner—Sang Paik
Attorney, Agent, or Firm—Fay, Sharpe, Fagan, Minnich & McKee, LLP

[57] ABSTRACT

A flash steam generator to be used as an integral component of a steam sterilizer. The generator is constructed of a metal block having a first bore drilled lengthwise through the metal block. Surrounding the first bore are a plurality of additional heater bores in which heating elements are inserted. The generator is integral to the sterilizer piping and control systems. Water is supplied to the first bore by the sterilizer piping system, and electricity is supplied to the heating elements by the sterilizer power supply. The heating elements convert the electricity to heat, which transfers via the metal block to the first bore where the heat rapidly boils the water contained therein in what is essentially a flash vaporization process.

12 Claims, 2 Drawing Sheets

INTEGRAL FLASH STEAM GENERATOR

FIELD OF INVENTION

This invention relates generally to a steam generator that quickly provides steam to a device requiring steam under pressure and that is integral with, but external to, the device. More particularly this invention relates to a flash steam generator integrated into a medical device sterilizer but not disposed within the sterilizer chamber.

BACKGROUND OF INVENTION

This invention relates to a steam generator for use in conjunction with a device, such as a medical device steam sterilizer, that requires a supply of pressurized steam. The generator and the device are integrated into a single unit so that the generator supplies steam directly to the portion of the device requiring the steam. When integrated with a steam sterilizer the generator supplies steam directly to the sterilizer jacket or chamber.

Certain types of devices, such as steam sterilizers, require pressurized steam for their operation. Some of these devices create steam by boiling water inside a chamber within the device, such as a sterilizer chamber, using an immersion heater. An immersion heater essentially is a large heating element usually located over the bottom surface of the chamber. An immersion heater has several disadvantages, however.

An immersion heater can be a relatively large piece of equipment. It works best when its wattage can be spread out over a large heating element surface area. This keeps the watt density low and extends the life of the heating element. This large heating element surface area, however, requires a lot of space and greatly increases the size of the steam generator and of the overall device when the generator is within the device.

An immersion heater also must have its heating element completely immersed in water. To remain immersed the large heating element thus requires a large volume of water—a much larger volume of water than the sterilizer needs to complete a sterilization cycle. This large volume of water must be disposed of at the end of each pressure pulse during a sterilizaton cycle, including at the end the entire sterilization cycle. Unified plumbing codes require that the water be cooled in a heat exchanger or mixed with cooling water before disposing it down a building drain. Also, a large volume of heated water requires a proportionately large amount of cooling water. Thus the disposal process consumes a substantial amount of water. Furthermore, due to the significant amount of chamber water required, an immersion heater used with a sterilizer increases the total length of the sterilization cycle because of the time required at the start of the cycle to bring the large volume of sterilizer chamber water up to boiling temperature to start generating steam.

An immersion heater also is prone to several service and reliability problems. The heater is prone to leaks where the heating element passes through the wall of the sterilizer chamber. The overtemperature protection device for the heater also must be inside the chamber, immersed in water or steam, and, therefore, its connections also must pass through the chamber wall creating additional potential leakage points. In addition, scale or mineral deposits build up on the heating element surface, reducing the heat transfer efficiency and heater life.

In contrast to using an immersion heater within a device, steam may be provided from a stand-alone boiler to the device requiring pressurized steam, such as a steam sterilizer. A stand-alone boiler is more costly than an immersion heater built into a device because it must be purchased as an entirely separate component from the device. In addition, a stand-alone boiler generally uses an immersion heater to produce steam, and, therefore, is prone to the same problems associated with that type of heater. In particular, the stand-alone boiler also requires time-consuming flushing procedures to clear mineral deposits that build up inside the boiler chamber.

The present invention provides a flash steam generator that is integral with a medical device steam sterilizer or other device requiring pressurized steam. Thus, it is less costly than a stand-alone boiler. In addition, in contrast to current steam sterilizers and stand-alone boilers, the steam generator of the present invention does not use an immersion heater to produce steam. The heating mechanism used in the present invention requires substantially less water, which decreases the sterilization cycle time and provides easier and more efficient water disposal. Furthermore, unlike an immersion heater, the heating mechanism of the present invention is not prone to leaks or the build up of scale or mineral deposits.

SUMMARY OF THE INVENTION

The present invention is a flash steam generator to be used as an integral component of a steam sterilizer or other device requiring a supply of pressurized steam. The generator comprises a metal block having a first bore drilled lengthwise, preferably through the center. Surrounding the first bore are additional lengthwise bores in which heating elements are inserted. The generator is integral to the sterilizer piping and control systems. Water is supplied to the first bore from the sterilizer piping system, and electricity is supplied to the heating elements by the sterilizer power supply. The heating elements convert the electricity to heat, which transfers via the metal block to the first bore where the heat rapidly vaporizes the contained water in what is essentially a flash vaporization process. An overtemperature device protects the system should the heating elements be energized without sufficient water in the block. A safety valve exists between the block and the sterilizer chamber to protect the block and the chamber from overpressure conditions. The block and connected piping are properly insulated to prevent heat loss to the atmosphere and accidental injury to the sterilizer operator.

DETAILED DESCRIPTION OF THE INVENTION

Figure 1:
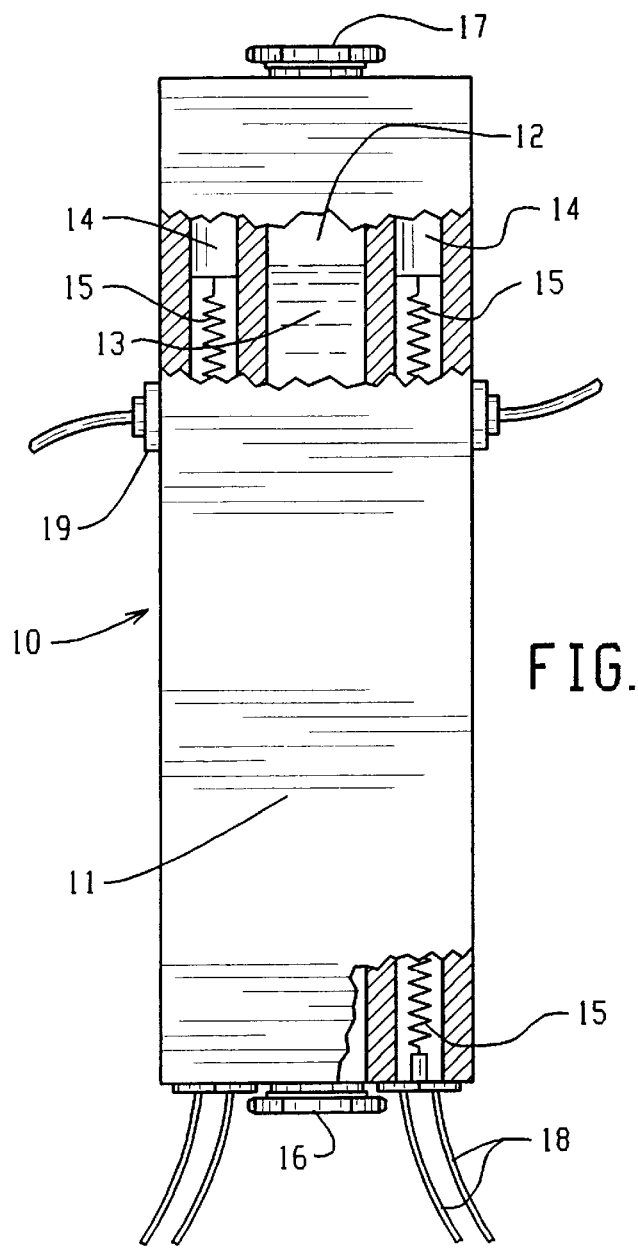
FIG. 1 is a side view of the integral flash steam generator of the present invention, with partial cut-away views showing internal features.

Referring now by reference numerals in the drawings, a preferred embodiment of the flash steam generator of the present invention is indicated generally by reference numeral 10. The generator comprises a block of metal 11, preferably carbon steel, although other heat-transferring metals may be used. The metal block 11 is mounted on the side of a steam sterilizer. The precise shape and dimensions may very depending upon the sterilzer, and the block may be sized and shaped to fit any common steam sterilizer or to accommodate any common heating elements. Preferably, the metal block is elongated into a rectangular prism and mounted vertically on the side of the sterilizer, although other shapes such as square blocks and cylinders may be used.

A first bore 12, preferably cylindrical in shape, is drilled through the entire length of the center of the metal block 11. As further described below, the first bore provides a chamber for receiving water 13 to be converted to steam. The first bore is sized to receive a volume of water that is sufficiently small to be vaporized rapidly in what amounts to essentially a flash vaporization process.

In addition to the first bore 12 are a plurality of heater bores 14, preferably drilled lengthwise through the metal block substantially parallel to the first bore. In the preferred embodiment, each heater bore 14 has a first bore end at the bottom of the metal block and a second bore end toward the top of the metal block. The heater bores 14 should extend at least substantially the entire length of the metal block, and preferably should extend through the entire metal block to permit easier access to the heater bores for maintenance purposes. The heater bores 14 are sized to receive a heating element 15. Electric cartridge heaters are particularly appropriate for use as the heating element in this device because they are commonly elongated and thin so that each heating element can be inserted into a heater bore and extend from the first bore end substantially to the second bore end.

Figure 2:
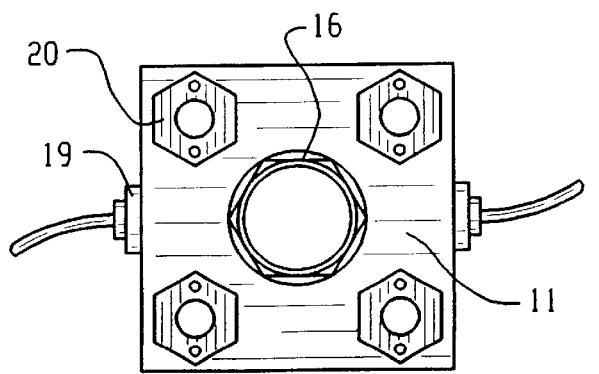
FIG. 2 is a bottom view of the generator shown in FIG. 1.

FIGS. 1 and 2 illustrate a preferred configuration of the heater bores 14, the electric cartridge heaters 15, and the first bore 12. In this preferred embodiment, the electric cartridge heaters are chosen to be thin enough so that the heater bores are narrow in comparision to the center bore. This ensures that there are a sufficient number of heating elements to create heat in an amount sufficient to vaporize the water contained in the first bore. FIG. 2 depicts a preferred embodiment having four heater bores 14, each containing an electric cartridge heater 15, surrounding the first bore 12 located in the center of the metal block. As seen in FIG. 2, the electric cartridge heaters may be mounted within the heater bores using screw plates 20, although other mechanisms to mount the heaters known in the art may be used. Note that any number and arrangement of heater bores and electric cartridge heaters may be incorporated into the metal block so long as sufficient heat can be generated by the heaters to produce steam.

The metal block 11 is fluidly connected to the sterilizer piping system 31,34. The metal block 11 comprises a bottom end having a first female NPT thread 16 extending downward from the first bore. This thread is a standard thread that will accept typical piping used with sterilizers. The first NPT thread connects the first bore to sterilizer piping 31 from which the first bore receives its supply of water. The metal block also comprises a top end having a second female NPT thread 17 extending upward from the first bore. The second NPT thread provides a fluid connection via piping 34 between the first bore 12 and the sterilization chamber 30, thereby permitting steam to be transferred from the generator water chamber to the sterilizer chamber for use during the sterilization cycle. In addition, each of the heating elements 15 is electrically connected to the sterilizer power supply by wires 18. Thus, the sterilizer power supply provides the electricity to the heating elements, which convert the electricity to heat for producing the steam.

Figure 3:
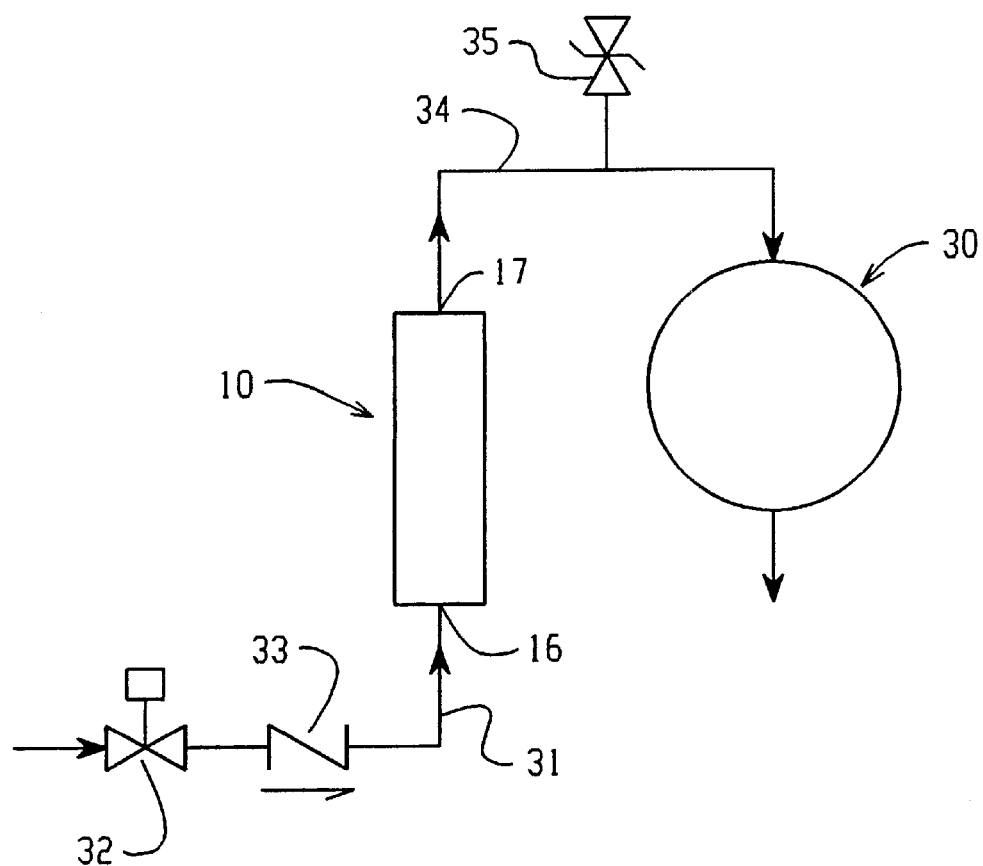
FIG. 3 is a schematic drawing of the flash steam generator of the present invention integrated into a sterilizer system.

FIG. 3 is a schematic depicting how the steam generator 10 is used integrally with a steam sterilizer 30. Water is supplied from sterilizer piping 31 through the first female NPT thread 16 to the first bore of the generator. The amount of water transferred to the generator is controlled by a solenoid valve 32 operated by the sterilizer control system, and is sufficiently small enough to be vaporized in what is essentially a flash vaporization process. The sterilizer piping system 31 also contains a check valve 33 to prevent the backflow of water out of the steam generator. The sterilizer control system also is used to control the flow of electricity from the sterilizer power supply to the heating elements 15. When the first bore 12 is injected with water 13 and the heating elements 15 are activated, heat transfers from the heating elements, through the metal block 11 to the first bore. The heat then flash vaporizes the water 13 located in the first bore 12 to produce steam. Then an additional amount of water is injected into the first bore and vaporized in the same manner.

The process continues in this manner, producing more steam from the series of water injections. As steam is produced, the pressure inside the first bore 12 increases. The steam is forced under pressure through the second female NPT thread 17, through a fluid pathway 34 connecting the generator 10 to the sterilization chamber 30, and into the sterilization chamber. The metal block 11 and the generator-to-chamber pathway are properly insulated to prevent heat loss to the atmosphere and human injury from inadvertent contact with the generator apparatus. The device also is equipped with two other safety features. An overtemperature device 19 is mounted on the metal block 11 and shuts down the heaters in the event the heaters are energized without sufficient water in the block. In addition, a safety release valve 35 is provided between the metal block 11 and the sterilization chamber 30 that can release excess pressure to protect the block and the chamber from overpressure conditions.

From the above description the advantages of the steam generator of the present invention are clear. Immersion heaters require that the heating element remain submerged in water at all times throughout the sterilization cycle. Due to the large surface area of immersion heaters, this requires substantially more water than that used in the series of water injections in the flash vaporization process of the present invention. The present invention, therefore, reduces total sterilization cycle time by reducing the initial start-up time required to produce steam. In addition, only a minimal amount of hot water remains for disposal between pulses in a sterilization cycle and/or at the end of the cycle. As stated above, unified plumbing codes require that any residual hot water be cooled in a heat exchanger or mixed with cooling water before disposing the water down a building drain. Because the present invention leaves only the smallest possible amount of residual hot water for disposal, less cooling water is required resulting in a substantial conservation of water.

The integral flash steam generator provides other advantages over an immersion heater or stand-alone boiler. In contrast to these other devices, the heating elements of the integral flash steam generator have no element portions submerged in water or steam that provide potential points of leakage. In addition, because the water never contacts the heating elements of the present invention, the heating elements are not prone to the build-up of scale or mineral deposits as are immersion heater elements.

The flash steam generator also provides the advantage of being integral with the sterilizer or other device. The generator receives its water from the sterilizer piping and operates under electronic control of the sterilizer control system. Thus it requires no additional piping or electronics to operate, making it less expensive to manufacture and install. The steam generator may be installed on the sterilizer at the manufacturing stage, or alternatively, provided as a sterilizer accessory to be retrofitted to the sterilizer as described above.

While a certain preferred embodiment of this invention has been described, it is understood by those skilled in the art that many modifications are possible without departing from the principles of this invention as defined in the claims that follow.

We claim:

1. A flash steam generator integral with a piping system and a electrical power supply of a medical device sterilizer comprising:

a block of metal having a first bore extending through the entire block and in fluid connection with the piping system to provide steam to said sterilizer, and a plurality of heater bores in thermal connection with the first bore, each said heater bore having a first bore end and a second bore end; and a plurality of heating elements in electrical connection with the power supply and in thermal connection with the heater bores, one each being mounted at the first bore end of each heater bore and extending through each heater bore toward the second bore end of each heater bore.

2. A flash steam generator according to claim 1 wherein the metal block comprises carbon steel.

3. A flash steam generator according to claim 2 wherein the metal block is elongated into a rectangular shaped block and mounted vertically on the side of the sterilizer.

4. A flash steam generator according to claim 1 wherein the heater bores extend through the metal block substantially parallel to the first bore and generally surround said first bore.

5. A flash steam generator according to claim 4 wherein the metal block contains four heater bores and four heating elements.

6. A flash steam generator according to claim 1 wherein the heating elements are electric cartridge heaters.

7. A flash steam generator according to claim 1 wherein the metal block includes an overtemperature device mounted on its side to protect the metal block from excess temperature conditions.

8. A flash steam generator according to claim 1 wherein the generator includes a pressure release valve mounted above the metal block to protect the metal block from excess pressure conditions.

9. A flash steam generator according to claim 1 wherein the generator includes an insulating material surrounding the metal block to prevent heat loss to the atmosphere.

10. A generator for providing a vaporized fluid substantially immediately to a device requiring pressurized vapor and being integral with a plurality of fluid conduits of said device, said generator comprising:

a main body consisting essentially of a metal block having at least one fluid passage forming a vaporization chamber, said fluid passage extending from a first end to a second end of said metal block to form a fluid connection with said fluid conduits, and a heater element in said block being thermally adjacent but not in contact with said fluid passage, whereby said fluid passage is controllably filled with a fluid from one said fluid conduit, heat is controllably thermally transferred from said heater element to said fluid in said fluid passage and vaporizing said fluid, and said vaporized fluid is transferred under pressure from said fluid chamber through another said fluid conduit to said device.

11. A system for sterilizing objects using pressurized steam comprising:

a sterilzier having a sterilization chamber, and having a piping system in fluid connection with an external water supply and in fluid connection with the sterilization chamber; and having an electrical power supply; and a flash steam generator integral with the piping system and electrical power suppy of the sterilizer comprising a block of metal having a first bore extending through the entire block and in fluid connection with the sterilizer piping system, and a plurality of heater bores in thermal connection with the first bore, each said heater bore having a first bore end and a second bore end; and a plurality of heating elements in electrical connection with the sterilizer power supply and in thermal connection with the heater bores, one each being mounted at the first bore end of each heater bore and extending through each heater bore toward the second bore end of each heater bore.

12. A flash steam generator integral with a piping system and an electrical power supply of a medical device sterilizer comprising:

a block of metal having a first bore extending through the entire block and in fluid connection with the sterilizer piping system, and a plurality of heater bores in thermal connection with the first bore, each said heater bore having a first bore end and a second bore end;

a plurality of heating elements in electrical connection with the sterilizer power supply and in thermal connection with the heater bores, one each being mounted at the first bore end of each heater bore and extending through each heater bore toward the second bore end of each heater bore wherein water flows into said first bore and steam is provided under pressure directly to a sterilizer jacket or chamber.

* * * * *